(12) United States Patent
Basilio et al.

(10) Patent No.: US 7,745,644 B2
(45) Date of Patent: Jun. 29, 2010

(54) ANTIBIOTIC COMPOUNDS

(75) Inventors: Angela Basilio, Madrid (ES); Olga Genilloud, Madrid (ES); Pilar Hernandez, Madrid (ES); Sheo Bux Singh, Edison, NJ (US); Jose Rueben Tormo, Madrid (ES); Jun Wang, Millburn, NJ (US)

(73) Assignees: Merck Sharp & Dohme Corp., Rahway, NJ (US); Merck Sharp and Dohme de Espana, S.A., Madrid (ES)

( * ) Notice: Subject to any disclaimer, the term of this patent is extended or adjusted under 35 U.S.C. 154(b) by 800 days.

(21) Appl. No.: 10/560,665

(22) PCT Filed: Jul. 20, 2004

(86) PCT No.: PCT/US2004/023780

§ 371 (c)(1),
(2), (4) Date: Dec. 13, 2005

(87) PCT Pub. No.: WO2005/009391

PCT Pub. Date: Feb. 3, 2005

(65) Prior Publication Data

US 2008/0306139 A1    Dec. 11, 2008

Related U.S. Application Data

(60) Provisional application No. 60/489,865, filed on Jul. 24, 2003.

(51) Int. Cl.
*C07D 311/00* (2006.01)
*C07D 493/00* (2006.01)
*A01N 43/00* (2006.01)
*A61K 31/33* (2006.01)

(52) U.S. Cl. ..................................... 549/212; 514/183
(58) Field of Classification Search ................. 549/212; 514/183
See application file for complete search history.

(56) References Cited

U.S. PATENT DOCUMENTS 6,365,610 B1    4/2002    Sasaki et al.

OTHER PUBLICATIONS

Karsi, A., Gülsoy, N., Corb, E., Dumpala, P.R., Lawrence, M.L. (2009) High-Throughput Bioluminescence-Based Mutant Screening Strategy for Identification of Bacterial Virulence Genes. Applied and Environmental Microbiology, vol. 75, No. 7, pp. 2166-2175.*
Hensel, M., Holden, D.W. (1996) Molecular genetic approaches for the study of virulence in both pathogenic bacteria and fungi. Microbiology, vol. 142, pp. 1049-1058.*
Kanbe, K., Mimura, Y., Tamamura, T., Yatagai, S., Sato, Y., Takahashi, A., Sato, K. (1992) AB3217-A, A Novel Anti-Mite Substance Produced by a Strain of *Streptomyces platensis*. The Journal of Antibiotics, vol. 45, No. 4, pp. 458-464.*
Singh, S.B. and coworkers. (2006) Isolation, Structure, and Absolute Stereochemistry of Platensimycin, A Broad Spectrum Antibiotic Discovered Using an Antisense Differential Sensitivity Strategy. The Journal of the American Chemical Scoiety, vol. 128, pp. 11916-11920.*
F. D. Lowry et al., "Antimicrobial Resistance: the example of *Staphylococcus aureus*", 2003, pp. 1265-1273, vol. 111, No. 9, J. of Clinical Investigation.
E. B. Shirling et al., "Methods for Characterization of *Streptomyces* Species", 1966, pp. 313-340, vol. 16, No. 3, International Journal of Systematic Bacteriology.

* cited by examiner

*Primary Examiner*—Shaojia Anna Jiang
*Assistant Examiner*—Scarlett Goon
(74) *Attorney, Agent, or Firm*—Baerbel R. Brown; Sylvia A. Ayler; John C. Todaro (57) ABSTRACT

Fermentation of a nutrient medium with a eubacterium *Streptomyces* sp. yields a novel antibacterial compound of structure (I).

5 Claims, 2 Drawing Sheets

FIG.2

ANTIBIOTIC COMPOUNDS

CROSS REFERENCE TO RELATED APPLICATIONS

This application is the National Stage of International Application No. PCT/US04/23780 filed on Jul. 20, 2004, which claims the benefit under 35 U.S.C. 119(e) of U.S. Provisional Applications No. 60/489,865 filed Jul. 24, 2003.

BACKGROUND OF TEE INVENTION

The present invention relates to a novel natural product that possesses antibacterial activity.

Infections caused by bacteria are a growing medical concern as many of these pathogens are resistant to various common antibiotics. Such microbes include *Staphylococcus aureus, Staphylococcus epidermidis, Staphylococcus hemolyticus, Streptococcus pyogenes, Streptococcus pneumoniae, Enterococcus faecalis, Enterococcus faecium, Pseudomonas aeruginosa, Actinobacter calcoaeticus, Escherichia coli* and *Stenotrophomonas maltophilia*. The antibiotic of this invention comprises an important contribution to therapy for treating infections that are resistant to various known antibiotics. For a review see: F. D. Lowy *The Journal of Clinical Investigation* 2003, 111 (9), 1265.

In the present invention, a novel natural product isolated from the eubacterial fermentation of *Streptomyces* sp. is described. This compound displays antibacterial activity against various pathogens, many of which have demonstrated resistance to currently available antibiotics.

SUMMARY OF THE INVENTION

This invention describes the novel natural product shown in formula I and its use as an antibacterial agent:

or a pharmaceutically acceptable salt thereof which is effective in the treatment of bacterial infections.

The invention is also concerned with a process for the production of Compound I by fermentation with the eubacterium, *Streptomyces* sp. The invention is also concerned with a process for isolating the compounds of Formula I from fermentation broths.

DETAILED DESCRIPTION OF THE INVENTION

This invention describes the compound of structural formula I:

or a pharmaceutically acceptable salt thereof.

The pharmaceutically acceptable salts of the compound of this invention include the conventional non-toxic salts as formed, from non-toxic inorganic or organic bases. For example, such conventional non-toxic salts include those derived from inorganic bases such as an alkali or alkaline earth metal hydroxide, e.g., potassium, sodium, lithium, calcium, or magnesium, and the like: and the salts prepared from organic bases such as an amine, e.g., dibenzylethylene-diamine, trimethylamine, piperidine, pyrrolidine, benzylamine and the like, or a quaternary ammonium hydroxide such as tetramethylammonium hydroxide and the like.

The pharmaceutically acceptable salts can be synthesized from the compounds of this invention by conventional chemical methods. Generally, the salts are prepared by reacting the free acid with stoichiometric amounts or with an excess of the desired salt-forming inorganic or organic base in a suitable solvent or various combinations of solvents.

Compound I of this invention displays antibiotic activity useful in the treatment of bacterial infections. It demonstrates antibacterial activity against various strains of *S. aureus, S. pneumoniae, E. faecalis, E. faecium, B. subtilis* and *E. coli* including species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolide-resistant *S. aureus* and *E. faecium*.

The compound of this invention can be formulated in pharmaceutical compositions by combining Compound I with a pharmaceutically acceptable carrier. Examples of such carriers are set forth below.

The compound may be employed in powder or crystalline form, in liquid solution, or in suspension. It may be administered by a variety of means; those of principal interest include: topically, orally and parenterally by injection (intravenously or intramuscularly).

Compositions for injection, one route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the Compound, the virulence of the infection and other factors. Such matters, however, are left to the routine discretion of the physician according to principles of treatment well known in the antibacterial arts.

The compositions for administration to humans per unit dosage, whether liquid or solid, may contain from about 0.01% to as high as about 99% of Compound I, one embodiment of the range being from about 10-60%. The composition will generally contain from about 15 mg to about 2.5 g of Compound I, one embodiment of this range being from about 250 mg to 1000 mg. In parenteral administration, the unit dosage will typically include pure Compound I in sterile water solution or in the form of a soluble powder intended for solution, which can be adjusted to neutral pH and isotonicity.

The invention described herein also includes a method of treating a bacterial infection in a mammal in need of such treatment comprising the administration of Compound I to the mammal in an amount effective to treat the infection.

One embodiment of the methods of administration of Compound I includes oral and parenteral methods, e.g., i.v. infusion, i.v. bolus and i.m. injection.

For adults, about 5-50 mg of Compound I per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000-2000 mg three to four times daily may be recommended.

For children, a dose of about 5-25 mg/kg of body weight given 2, 3, or 4 times per day is preferred; a dose of 10 mg/kg is typically recommended.

Another aspect of this invention is the process for producing Compound I, which comprises cultivating a *Streptomyces* sp. microorganism in a suitable nutrient medium and then recovering the compound of this invention from the fermentation broth. There are two organisms in question, ATCC#PTA-5316 (MA7327) and ATCC#PTA-5317 (MA7331) identified as the eubacterium, *Streptomyces* sp. following taxonomic studies and deposited in the Merck Culture Collection.

The organisms were subsequently placed on permanent deposit with the Amercian Type Culture Collection (ATCC), 12301 Parklawn Drive, Rockville, Md., 20852 and have been assigned accession numbers ATCC# PTA-5316 (Merck# MA7327) and ATCC#PTA-5317 (Merck# MA7331).

Any restrictions relating to public access to the microorganism shall be irrevocably removed upon patent issuance. Although the use of these particular species is described in connection with this invention, there may be other species and mutants of the above organism capable of producing Compound I, and their use is contemplated in carrying out the process of this invention.

The compound of structural Formula I is produced by the aerobic fermentation of a suitable medium under controlled conditions via inoculation with a culture of the eubacterium, *Streptomyces* sp. The suitable medium is preferably aqueous and contains sources of assimilable carbon, nitrogen, and inorganic salts.

The medium employed for fermentation by the *Streptomyces* sp. is primarily the well-known Difco Tryptic Soy Broth, either alone or with added nutrients commonly used by those skilled in the art.

It should be noted that the nutrient media described herein are merely illustrative of the wide variety of media which may be employed and are not intended to limit the scope of this invention in any way.

The fermentation is conducted at temperatures ranging from about 10° C. to about 40° C.; however for optimum results it is preferred to conduct the fermentation at about 28° C. The pH of the nutrient medium during the fermentation can be about 5.5 to about 7.5.

It is to be understood that for the fermentative production of the compound of this invention, the invention is not limited to the use of the particular *Streptomyces* sp. with ATCC accession numbers, ATCC# PTA-5316 (Merck# MA7327) and ATCC#PTA-5317 (Merck# MA7331). It is especially desired and intended that there be included in the scope of this invention the use of other natural or artificial mutants produced or derived from the described cultures, or other variants or species of the *Streptomyces* genus insofar as they can produce the compound of this invention. The artificial production of mutant species or strains of *Streptomyces* from ATCC# PTA-5316 (Merck# MA7327) and ATCC#PTA-5317 (Merck# MA7331) may be achieved by conventional, physical or chemical mutagens, for example, ultraviolet irradiation of the described culture, or nitrosoguanidine treatment and the like. Recombinant DNA techniques such as protoplast fusion, plasmid incorporation, chromosome fragment incorporation and the like also may prove useful.

EXAMPLE 1

Production of Compound I

Same Method Applied for Both ATCC#PTA-5316 (MA7327) and ATCC#PTA-5317 (MA7331)

| Media composition: | |
| --- | --- |
| Seed Medium | g/L |
| Soluble Starch | 20.0 |
| Dextrose | 10.0 |
| NZ Amine Type E | 5.0 |
| Beef Extract | 3.0 |
| Yeast Extract | 5.0 |
| Peptone | 5.0 |
| (pH adjust to 7.0) | |
| Calcium Carbonate | 1.0 |
| CLA (Corn meal Lactose Ardamine) | (Production Medium, per L) |
| Amberex pH | 5.0 g |
| Yellow Corn Meal | 40.0 g |
| Lactose | 40.0 g |
| P-2000 (antifoaming agent) | 1.0 mL |

A frozen suspension (2.0 mL) of a *Streptomyces* sp. ATCC# PTA-5316 (MA7327) was inoculated into a 250 mL baffled flask containing 50 mL of seed medium. The flask was incubated at 28.0° C. with an agitation of 220 RPM for 48 hours. The second stage seed was developed by inoculating 10 mL, of the first stage seed into a two liter non-baffled shake flask containing 500 mL of seed medium. The flask was incubated at 28.0° C. with an agitation of 180 RPM for 48 hours. A 75 liter scale Chemap fermenter containing 50 liters of the CLA production medium was inoculated with 1.5 liters from the second stage seed. Operating parameters for the 75 liter scale fermenter were: Temperature=28° C., Agitation=300 RPM, Airflow=30 slpm, and pressure=5 psig. The fermenter containing 43 L of broth was harvested after 9 days of incubation.

Isolation of compound I: To a 43 L fermentation broth was added 29 L MeOH and was acidified to pH 3.0 to give a final volume of 72 L. This extract was filtered and the filtrate was directly charged on a 1.5 L amberchrome and eluted with a 40-100% aqueous MeOH gradient collecting 600 mL each fractions. Fractions 11-13 containing mainly compound I were pooled and concentrated to 200 mL mainly aqueous, which was diluted with 300 mL water to give a final volume of 500 mL. Solid sodium bicarbonate was added to raise the pH to 9.0. This solution was extracted three times with equal volumes of methylene chloride. The aqueous layer was acidified to pH 2.0 with 6 N HCl (hydrochloric acid) and extracted four times with equal volumes of methylene chloride and the combined extract (1900 cc) were concentrated to 2.6 g of semi-purified compound I.

The semi-purified material was dissolved in small volume of ethyl acetate and charged to a 500 cc silica gel column packed in 80:20; hexane-ethyl acetate. The column was washed with four column volumes of the hexane-ethyl acetate (8:2) followed by four column volumes of 80:20:0.5:0.5:0.5 of ethyl acetate:hexane:water:glacial acetic acid:methanol collecting 200 mL each fractions. Fractions 6-10 were pooled, concentrated under reduced pressure to give 1.24 g of compound I.

Large scale isolation procedure of compound I: A 5 liters fermentation broth was acidified with 4 N HCl and extracted with 2.5 liters of isopropyl acetate which was extracted with 300 ml of 5% aqueous solution of sodium bicarbonate. The bicarbonate layer was charged to a 150 mL amberchrome column and washed with water until pH of eluents were neutral. The column was washed with one column volume of 0.1N HCl and washed with water until the pH of eluents became neutral. The column was eluted with two column volumes each of 20, 40, 60, 80, 90 and 100% aqueous methanol. The compound I eluted in the 90 and 100% aqueous methanol fractions. The pooled fractions were concentrated under reduced pressure mainly to aqueous and extracted with equal volumes of methylene chloride (isopropyl acetate and ethyl acetate were equally effective). The organic layer was concentrated to dryness to afford 193 mg of compound I as an amorphous powder, which could be crystallized from hot nitromethane, isopropyl acetate, ethyl acetate or acetonitrile-water.

Physical data of compound I: crystallized from nitromethane as buff colored needles, mp 220-223° C. (decomposition at 230° C.), UV (CH$_3$OH) $\lambda_{max}$ 227 ($\epsilon$ 28,167), 296 (4,825) nm, $[\alpha]^{23}{}_D$-51.1° (c 0.135, CH$_3$OH), FTIR (ZnSe) 3400, 2964, 1713 (w), 1650, (br, strong), 1535, 1446, 1378, 1296, 1240, 1153, 1105, 1091, 1024, 953, 828, 791, 608 cm$^{-1}$, HEESIFTMS: Found: 442.1853; calcd for C$_{24}$H$_{27}$NO$_7$+H: 442.1866, $^1$H NMR (500 MHz) C$_5$D$_5$N $\delta_H$: 1.14 (3H, s), 1.40 (3H, s), 1.48 (3H, d, J=11 Hz), 1.57 (1H, dd, J=11.5, 6.5 Hz), 1.73 (1H, dd, J=10.5, 3 Hz), 1.81 (2H, brd, J=11.5 Hz), 1.90 (1H, m), 2.0 (1H, m), 2.20 (1H, t, J=6.5 Hz), 2.45 (1H, brs), 2.68 (1H, m), 2.75 (1H, ddd, J=14.5, 11.5, 5), 2.83 (1H, ddd, J=14.5, 11.5, 5.5 Hz), 4.49 (1H, t, J=3.5 Hz), 5.94 (1H, d, J=10 Hz), 6.37 (1H, d, J=10 Hz), 6.87 (1H, d, J=9 Hz), 8.12 (1H, d, J=9 Hz), 10.5 (1H, s);

$^{13}$C NMR (125 MHz) C$_5$D$_5$N $\delta_C$: 23.9, 25.1, 32.4, 32.8, 41.4, 43.7, 45.7, 46.8, 47.2, 47.4, 55.6, 77.1, 87.5, 107.8, 110.5, 115.9, 127.9, 130.1, 154.6, 158.5, 159.1, 175.0, 175.2, 203.8

Characterization of Culture

Observations of growth, general cultural characteristics and carbon source utilization were made in accordance with the methods of Shirling and Gottlieb (*Int. J. Syst. Bacteriol.* (1966) 16: 313-340). Coloration of the cultures was determined by comparison with color standards contained in the Methuen Handbook of Colour (A. Kornerup and J. H. Wauscher, Third Edition, 1978).

Chemical composition of the cells was determined using the methods of Lechevalier and Lechevalier (1980).

Fatty acid composition was determined using a modified sample preparation (Sasser, 1990). Analysis of fatty acid methyl esters (FAMEs) was carried out by capillary gas chromatography using a Hewlett Packard Model 6890N gas chromatograph/Microbial Identification System software (MIDI, Inc., Newark, Del.) equipped with a phenyl methyl silicone column (0.2 mm×25 m). Individual fatty acids identification was determined by the Microbial Identification System software.

The complete 16S rDNA sequence was determined from the 1500 bp PCR fragment obtained using primers 27f and 1525r (Lane, 1991). The PCR product was used as template in sequencing reactions using an ABI PRISM™ Dye Terminator Cycle sequencing Kit (Perkin Elmer). Partial sequences were assembled using the GCG Fragment Assembly System (Wisconsin Package, version 8) and sequences were aligned with the program CLUSTALW (Intelligenetics, Inc.). The phylogenetic analysis of the aligned sequences was performed using the maximum-parsimony analysis with the branch-and-bound algorithm of the Phylogeny Using Parsimony Analysis (PAUP) program version 4.0. (Swofford, 1993).

Source:

The strain The strain ATCC# PTA-5316 (MA7327) was obtained from a soil collected in Eastern Cape, South Africa. The soil sample was associated to the rhyzosphere of *Manulea obovbata*, in a coastal zone of fynbos and dunes. The strain was isolated after serial dilution of the soil sample and plating on starch casein agar containing 20 ug/ml nalidixic acid.

The strain ATCC#PTA-5317 (MA7331) was isolated from a soil collected in Mallorca, Balearic Islands, Spain. The strain was isolated after pretreatment of the soil with 0.01% benzethonium chloride and plating on humic-acid based agar supplemented with 20 ug/ml novobiocin.

General Growth Characteristics.

Strain ATCC PTA-5316 (MA7327) grows well on a range of agar media such as Yeast Malt Extract, Oatmeal, Glycerol Asparagine, Inorganic Salts Starch and Trypticase Soy agars at 28° C. The gross colonial morphology is typical of streptomycetes and its growth characteristics, including spore-mass colour, substrate mycelial pigmentation and the production of different pigments were recorded in different agar media (Table 1).

Colony morphology (on Yeast Malt Extract Agar, ISP2): Substrate mycelium initially whitish yellow turns brownish orange (5C6) after 21 days of incubation. The initial white aerial mycelium continues to develop after 21 days incubation turning yellow grey to finally become grey (5D2) with brownish wet exudate droplets.

Micromorphology: the spore-chain morphology was examined directly on the plates by light microscopy under 400× and 1000× magnification. Observations were made after 7, 14 and 21 days of cultivation on Yeast Malt Extract agar. The aerial mycelium arises from extensive branched substrate hyphae. Sparse branched aerial hyphae differentiate initially into short and irregular tight spore chain spirals. Sporophores are formed by less than 10-20 spores and with time tend to coalesce in a dark mucous mass of spores in older cultures. Similar morphologies were observed in most of the other test media but with different degrees of coalescence. On the contrary in the glycerol asparagines agar the strain grows as a sterile vegetative mycelium.

Strain ATCC#PTA-5317 (MA7331) grows well on the agar media tested such as Yeast Malt Extract, Oatmeal, Glycerol Asparagine, Inorganic Salts Starch and Trypticase Soy agars at 28° C. The gross colonial morphology is typical of streptomycetes and its growth characteristics were recorded in different agar media (Table 1).

Colony morphology (on Yeast Malt Extract Agar, ISP2): Substrate mycelium initially whitish yellow turns yellowish brown (5E7) after 21 days of incubation. The initial yellowish white aerial mycelium continues to develop after 21 days incubation to become uniformly grey (5E1).

Micromorphology: the spore-chain morphology was examined directly on the plates by light microscopy under 400× and 1000× magnification. Observations were made after 7, 14 and 21 days of cultivation on Yeast Malt Extract agar. An extensive aerial mycelium arises from a branched substrate hyphae. Sporophores are born at tip of aerial hyphae or in secondary branching hyphae. They form short and tight irregular spore chains with loop or coils, that after longer incubation time coalesce. Similar morphologies with different degrees of coalescence were observed in the other test media excepting in glycerol asparagine agar where the strain grows as a sterile vegetative mycelium.

Chemotaxonomic analysis.

The analysis of cell wall composition shows that strains ATCC# PTA-5316 (MA7327) and ATCC#PTA-5317 (MA7331) contain LL-$A_2$pm in whole-organism hydrolysates, a characteristic of *Streptomyces*. Strain ATCC# PTA-5316 (MA7327) contains glucose as major cell wall sugar whereas glucose and galactose are found as characteristic sugars in strain ATCC#PTA-5317 (MA7331). Both strains are rich in saturated straight-chain and iso- and anteiso-fatty acids but present completely different fatty acid patterns. Complete fatty acid compositions of are given in Table 2. The predominant fatty acids found in whole-cell methanolysates correspond to 15:0 anteiso and 16:0 iso, which are also typical of *Streptomyces*. All these chemotaxonomic analyses indicate that both strains correspond to members of the genus *Streptomyces*.

Physiological Properties.

The strains present slightly different carbon utilization patterns (Table 3):

ATCC# PTA-5316 (MA7327): good utilization of D-glucose, sucrose, 1-inositol, D-mannitol, D-fructose and raffinose; moderate utilization of D-xylose; poor utilization of L-arabinose and cellulose and no utilization of rhamnose.

ATCC#PTA-5317 (MA7331): good utilization of sucrose, D-xylose, I-inositol, D-fructose and raffinose; moderate utilization of D-glucose and D-mannitol; poor utilization of L-arabinose and no utilization of cellulose and rhamnose.

16S rDNA Sequence and Phylogenetic Analysis.

Figure 1:
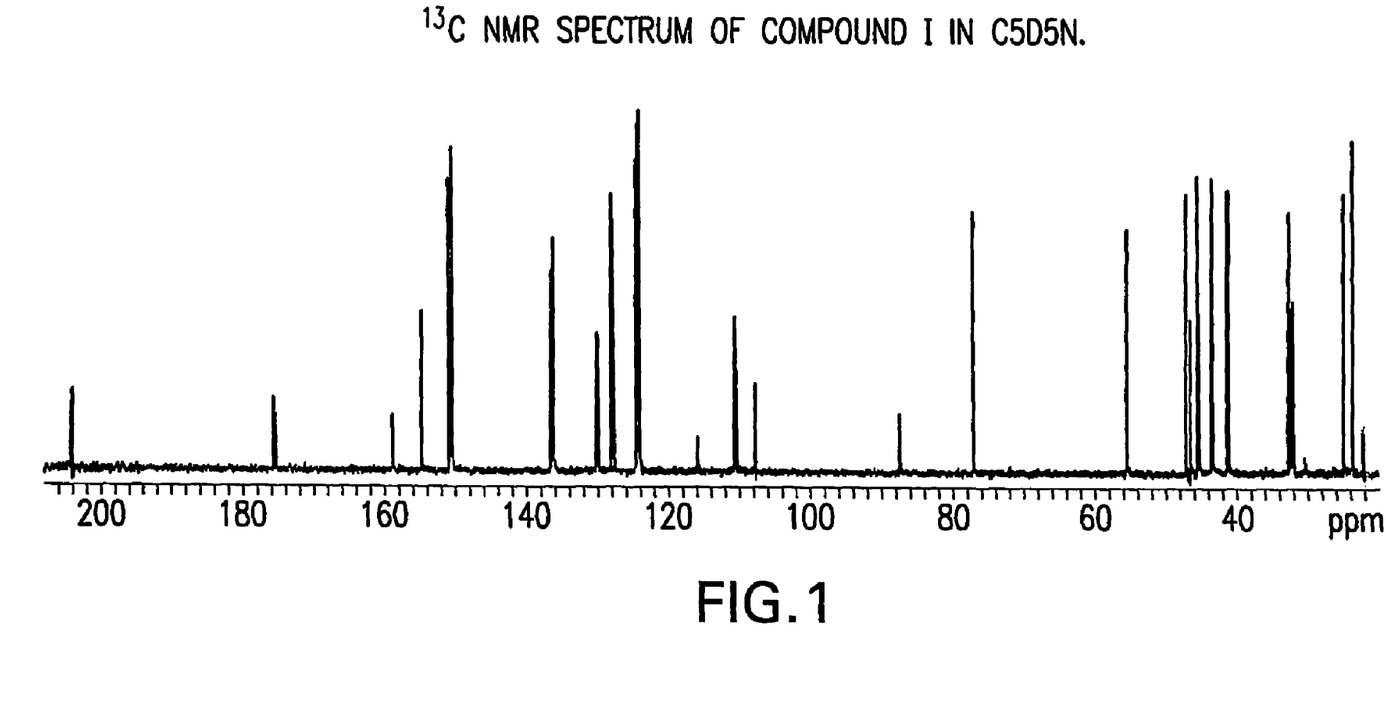
FIG. 1 is a $^{13}C$ NMR spectrum of Compound I in $C_5D_5N$.
Figure 2:
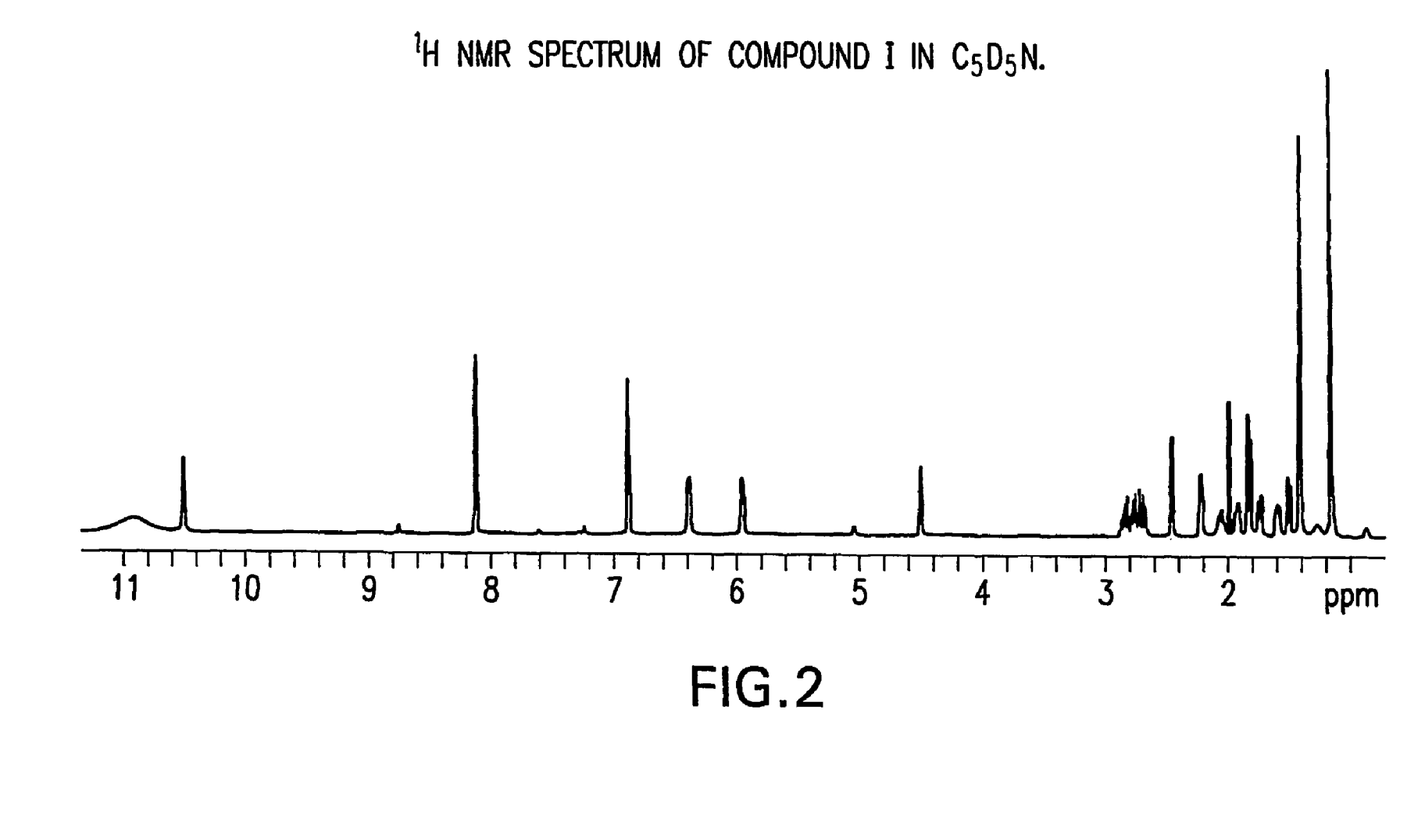
FIG. 2 is a $^1H$ NMR spectrum of Compound I in $C_5D_5N$.

The complete 16S rDNA sequence has been determined for both strains (FIG. 2). Sequences were aligned with *Streptomyces* nucleotide sequences from Genbank (AB045882) and the taxonomic position of both strains was determined by phylogenetic analysis of the aligned 16S rDNA sequences of 126 validated *Streptomyces* species. A phylogenetic tree based on these 16S rDNA sequences was built using the maximum parsimony method. Bootstrap replicates from each grouping was used as a measure of statistical confidence. A grouping found on 95% of bootstrap replicates was considered statistically significant.

The strains ATCC# PTA-5316 (MA7327) and ATCC#PTA-5317 (MA7331) appear in the same branch associated to the strain *Streptomyces platensis* ATCC 13865. This close relationship is highly supported by the bootstrapping value (92%) and suggests that both isolates can be identified by different strains of the species *Streptomyces platensis*.

TABLE 1

Cultural characteristics of *Streptomyces* sp. ATCC# PTA-5316(MA7327) and ATCC#PTA-5317(MA733 (21 days, 28° C.)

| Medium | Amount of growth | Aerial Mycelium | Soluble pigments | Substrate Mycelium |
|---|---|---|---|---|
| Strain ATCC#PTA-5316(MA7327) | | | | |
| Yeast Extract Malt Extract (ISP2) | Abundant | Birch grey (5D2) with brown spots (5F4); extended aerial hyphae with very few short spore spirals | None | Brownish orange (5C6) |
| Oatmeal (ISP3) | Abundant | Grey (5D2) with extended brownish coalescence (5F4); Short sporophores arranged in tight short spirals (4-5 loops) on highly branched aerial mycelium | None | Yellowish brown (5E8) |
| Inorganic Salts Starch (ISP4) | Abundant | Grey (5D2) with extended brownish coalescence of spore mass (5F4); extended | None | Yellowish white in the borders (4A2) with |

TABLE 1-continued

Cultural characteristics of *Streptomyces* sp. ATCC# PTA-5316(MA7327) and ATCC#PTA-5317(MA733 (21 days, 28° C.)

| Medium | Amount of growth | Aerial Mycelium | Soluble pigments | Substrate Mycelium |
|---|---|---|---|---|
| Glycerol Asparagine (ISP5) | Sparse | coalescence impairs observation of spore spirals. none | None | brownish grey center (4E2) Orange grey (5B2) sterile vegetative mycelium |
| Tyrosine Agar (ISP7) | Abundant | Yellowish brown in the edges and grey in the center (5B1); abundant short spore spirals in branched aerial hyphae | None | Dark brown (6F8) |
| Strain ATCC#PTA-5317 (MA7331) | | | | |
| Yeast Extract Malt Extract (ISP2) | Abundant | Uniformly grey (5E1), dense growth, extensive aerial mycelium with short and tight irregular spore chains forming loops and coils. Sporophores born in main and secondary aerial branches, coalescence. | None | Yellowish brown (5E7) |
| Oatmeal (ISP3) | Abundant | Brownish grey (5F2), extensive aerial mycelium, coalescence of spore chains. | None | Olive brown (4E4) |
| Inorganic Salts Starch (ISP4) | Abundant | Brownish grey (5F2), extensive aerial mycelium, coalescence of spore chains. | None | Olive brown (4D3/E3) |
| Glycerol Asparagine (ISP5) | Sparse | none | None | White(4B2), sterile substrate mycelium |
| Tyrosine Agar (ISP7) | Abundant | Grey (5C1), extensive aerial mycelium growth, short and tight spirals up to 3 turns born in main aerial hyphae, collapsing in coalescence | none | Greyish yellow (4B4) |

TABLE 2

Major fatty acids found in strains ATCC# PTA-5316 (MA7327) and ATCC#PTA-5317 (MA7331)

| Fatty acid | % of total fatty acids MA7327 | % of total fatty acids MA7331 |
|---|---|---|
| 14:0 iso | 11.54 | 2.50 |
| 15::0 | 2.14 | 4.12 |
| 15:0 iso | 8.95 | 25.02 |
| 15:0 anteiso | 14.77 | 11.25 |
| 15:0 anteiso 20H | 8.71 | 3.22 |
| 16::0 | 1.72 | 4.78 |
| 16:0 iso | 26.19 | 14.23 |
| 16:1 iso H | 7.78 | 2.15 |
| 16:0 iso 20H | 2.07 | 0.00 |
| 17:0 | 0.00 | 0.81 |
| 17:0 anteiso | 3.56 | 5.59 |
| 17:0 cyclo | 0.97 | 2.32 |
| 17:0 iso | 1.35 | 7.72 |
| 17:0 iso 20H | 0.00 | 0.73 |
| 17:1 iso C | 1.43 | 4.28 |
| 17:1 anteiso C | 2.67 | 2.01 |
| 17:1 cis9 | 0.00 | 0.73 |

TABLE 3

Carbohydrate utilization patterns of strains ATCC# PTA-5316 (MA7327) and ATCC#PTA-5317 (MA7331)

| Carbon source | MA7327 | MA7331 |
|---|---|---|
| D-glucose | 3 | 2 |
| L-arabinose | 1 | 1 |
| Sucrose | 3 | 3 |
| D-xylose | 2 | 3 |
| I-inositol | 3 | 3 |
| D-mannitol | 3 | 2 |
| D-fructose | 3 | 3 |
| Rhamnose | 0 | 0 |
| Raffinose | 3 | 3 |
| Cellulose | 1 | 0 |

Growth of the culture was monitored using compounds in the table as a carbon source: Observations were made at 7, 14 and 21 days intervals and 28° C. and utilization of the respective carbon sources are listed below. Growth levels: 3=good utilization; 2=moderate utilization; 1=poor utilization; 0=no utilization.

FIG. 2. 16S rDNA Sequences of Strains ATCC# PTA-5316 (MA7327) and ATCC#PTA-5317 (MA7331) and the Sequence in Database Strain ATCC#PTA-5316 (MA7327) 16S rDNA region
(from: 1 to: 1449)

SEQ. ID. No. 1

```
   1 CCGTCAGGAC GGACGCTGGC GGCGTGCTTA ACACATGCAA GTTCCAACGA
  51 TGAACCTCCT TCGGGAGGGG AATTAGTGGC GAACGGGTGA GTAACACGTG
 101 GGCAATCTGC CCTTCACTCT GGGACAAGCC CTGGAAACGG GTCTAATAC
 151 CGGATACGAC CACCGACCGC ATGGTCGTGG TGGTGGAAAG CTCCGGCGGT
 201 GAAGGATGAG CCCGCGGCCT ATCAGCTTGT TGGTGGGGTG ATGGCCTACC
 251 AAGGCGACGA CGGGTAGCCG GCCTGAGAGG GCGACCGGCC ACACTGGGAC
 301 TGAGACACGG CCCAGACTCC TACGGGAGGC AGCAGTGGGG AATATTGCAC
 351 AATGGGCGAA AGCCTGATGC AGCGACGCCG CGTGAGGGAT GACGGCCTTC
 401 GGGTTGTAAA CCTCTTTCAG CAGGGAAGAA GCGAGAGTGA CGGTACCTGC
 451 AGAAGAAGCG CCGGCTAACT ACGTGCCAGC AGCCGCGGTA ATACGTAGGG
 501 CGCAAGCGTT GTCCGGAATT ATTGGGCGTA AAGAGCTCGT AGGCGGCTTG
 551 TCACGTCGGA TGTGAAAGCC CGGGGCTTAA CCCCGGGTCT GCATTCGATA
 601 CGGGCAGGCT AGAGTTCGGT AGGGGAGATC GGAATTCCTG GTGTAGCGGT
 651 GAAATGCGCA GATATCAGGA GGAACACCGG TGGCGAAGGC GGATCTCTGG
 701 GCCGATACTG ACGCTGAGGA GCGAAAGCGT GGGGAGCGAA CAGGATTAGA
 751 TACCCTGGTA GTCCACGCCG TAAACGTTGG GAACTAGGTG TGGGCGACAT
 801 TCCACGTCGT CCGTGCCGCA GCTAACGCAT TAAGTTCCCC GCCTGGGGAG
 851 TACGGCCGCA AGGCTAAAAC TCAAAGGAAT TGACGGGGGC CCGCACAAGC
 901 AGCGGAGCAT GTGGCTTAAT TCGACGCAAC GCGAAGAACC TTACCAAGGC
 951 TTGACATACA CCGGAAACGT CTGGAGACAG CGCCCCCTT GTGGTCGGTG
1001 TACAGGTGGT GCATGGCTGT CGTCAGCTCG TGTCGTGAGA TGTTGGGTTA
1051 AGTCCCGCAA CGAGCGCAAC CCTTGTTCTG TGTTGCCAGC ATGCCCTTCG
1101 GGGTGATGGG GACTCACAGG AGACTGCCGG GGTCAACTCG GAGGAAGGTG
1151 GGGACGACGT CAAGTCATCA TGCCCCTTAT GTCTTGGGCT GCACACGTGC
1201 TACAATGGCC GGTACAATGA GCTGCGATAC CGCGAGGTGG AGCGAATCTC
1251 AAAAAGCCGG TCTCAGTTCG GATTGGGGTC TGCAACTCGA CCCCATGAAG
1301 TCGGAGTTGC TAGTAATCGC AGATCAGCAT TGCTGCGGTG AATACGTTCC
1351 CGGGCCTTGT ACACACCGCC CGTCACGTCA CGAAAGTCGG TAACACCCGA
1401 AGCCGGTGGC CACAACGCCC TCTGTGCGAG GCAATCTGTC CGAAGGTCG
```

Strain ATCC#PTA-5317 (MA7331) 16S rDNA region
(from: 1 to: 1496)

SEQ. ID. No. 2

```
   1 TCCTGGCTCA GGACGAACGC TGGCGGCGTG CTTAAACACA TGCAAGTCGA
  51 ACGATGAACC TCCTTCGGGA GGGGATTACT GGCGAACGGG TGAGTAACAC
 101 GTGGGCAATC TGCCCTTCAC TCTGGGACAA GCCCTGGAAA CGGGGTCTAA
 151 TACCGGATAC GACACACGAC CGCATGGTCT GTGTGTGGAA AGCTCCGGCG
 201 GTGAAGGATG AGCCCGCGGC CTATCAGCTT GTTGGTGGGG TGATGGCCTA
 251 CCAAGGCGAC GACGGGTAGC CGGCCTGAGA GGGCGACCGG CCACACTGGG
 301 ACTGAGACAC GGCCCAGACT CCTACGGGAG GCAGCAGTGG GGAATATTGC
 351 ACAATGGGCG AAAGCCTGAT GCAGCGACGC CGCGTGAGGG ATGACGGCCT
```

```
                          -continued
 401  TCGGGTTGTA AACCTCTTTC AGCAGGGAAG AAGCGAGAGT GACGGTACCT

451  GCAGAAGAAG CGCCGGCTAA CTACGTGCCA GCAGCCGCGG TAAATAACGT

501  AGGGCGCAAG CGTTGTCCGG AATTATTGGG CGTAAAGAGC TCGTAGGCGG

551  CTTGTCACGT CGGATGTGAA AGCCCGGGGC TTAACCCCGG GTCTGCATTC

601  GATACGGGCA GGCTAGAGTT CGGTAGGGGA GATCGGAATT CCTGGTGTAG

651  CGGTGAAATG CGCAGATATC AGGAGGAACA CCGGTGGCGA AGGCGGATCT

701  CTGGGCCGAT ACTGACGCTG AGGAGCGAAA GCGTGGGGAG CGAACAGGAT

751  TAGATACCCT GGTAGTCCAC GCCGTAAACG TTGGGAACTA GGTGTGGGCG

801  ACATTCCACG TCGTCCGTGC CGCAGCTAAC GCATTAAGTT CCCCGCCTGG

851  GGAGTACGGC CGCAAGGCTA AAACTCAAAG GAATTGACGG GGGCCCGCAC

901  AAGCAGCGGA GCATGTGGCT TAATTCGACG CAACGCGAAG AACCTTACCA

951  AGGCTTGACA TACACCGGAA ACGTCTGGAG ACAGGCGCCC CCTTGTGGTC

1001  GGTGTACAGG TGGTGCATGG CTGTCGTCAG CTCGTGTCGT GAGATGTTGG

1051  GTTAAGTCCC GCAACGAGCG CAACCCTTGT TCTGTGTTGC CAGCATGCCC

1101  TTCGGGGTGA TGGGGACTCA CAGGAGACTG CCGGGGTCAA CTCGGAGGAA

1151  GGTGGGGACG ACGTCAAGTC ATCATGCCCC TTATGTCTTG GGCTGCACAC

1201  GTGCTACAAT GGCCGGTACA ATGAGCTGCG ATACCGCGAG GTGGAGCGAA

1251  TCTCAAAAAG CCGGTCTCAG TTCGGATTGG GGTCTGCAAC TCGACCCCAT

1301  GAAGTCGGAG TTGCTAGTAA TCGCAGATCA GCATTGCTGC GGTGAATACG

1351  TTCCCGGGCC TTGTACACAC CGCCCGTCAC GTCACGAAAG TCGGTAACAC

1401  CCGAAGCCGG TGGCCCAACC CCTTGTGGGA GGGAATCGTC GAAGGTGGGA

1451  CTGGCGATTG GGACGAAGTC GTAACAAGGT AGCCGTACCG GAAGGT
```

The protocols used to determine the antibacterial activity of Compound I are described below.

Materials:

Cation-Adjusted Mueller Hinton Broth (MH; BBL)

50% Lysed Horse Blood (LHB; BBL) (stored frozen)

RPMI 1640 (BioWhittaker)

Human Serum (Pel-Freez)

RPMI 1640 (BioWhittaker)

*Haemophilus* Test Medium (HTM, Remel)

Trypticase Soy Broth (TSB, 5 mL/tube; BBL)

0.9% Sodium Chloride (Saline; Baxter)

Trypticase Soy+5% Sheep Blood Agar Plates (TSA; BBL)

Sabouraud Dextrose Agar Plates (BBL)

Chocolate Agar Plates (BBL)

2× Skim Milk (Remel)

Microbank Beads (Kramer Scientific)

MIC 2000 Microtiter plate inoculator.

2× Trypticase Soy Broth (TSB, BBL)+15% glycerol/50% horse serum.

96-Well Microtiter plates, lids, inoculum trays (Dynex Laboratories)

8-Channel Finn Multichannel pipettor, 0.5-10 µL volume

Methods:

Media Preparation

Cation-Adjusted Mueller Hinton Broth (BBL): Prepared according to manufacturer's instructions (22 gms dissolved in 1000 mL water, autoclaved 22 minutes). Stored refrigerated. Filter-sterilized before use using a Corning 0.45 Tm cellulose acetate filter.

50% Lysed Horse Blood: Defibrinated horse blood is diluted 1:1 with sterile distilled water; frozen, thawed and re-frozen (at least 7 times), then centrifuged. Stored frozen at −20° C.

Cation-Adjusted Mueller Hinton+2.5% Lysed Horse Blood: Aseptically add 5 mL 50% lysed horse blood to 100 mL Cation-Adjusted Mueller Hinton Broth. Filter-sterilize before use using a Corning 0.45 Tm cellulose acetate filter.

Cation-Adjusted Mueller Hinton+50% Human Serum: Aseptically add 50 mL Human Serum to 50 mL 2× Cation-Adjusted Mueller Hinton Broth. Filter-sterilize before use using a Corning 0.45 Tm cellulose acetate filter.

*Haemophilus* Test Medium (Remel): Received prepared from manufacturer. Filter-sterilized before use using a Corning 0.45 Tm cellulose acetate filter.

0.9% Sodium Chloride (Saline; Abbott Labs): Received prepared from manufacturer.

2× Skim Milk (Remel): Received prepared from manufacturer.

All agar plates are received prepared from manufacturer.

Preparation of Compounds

The compounds are prepared on a weight basis. Compounds are prepared to 2 mg/mL in 100% DMSO, then

| Conditions and Inoculum for Representative Strains | |
| --- | --- |
| Bacillus, Staphylococcus, Enterococcus: Escherichi:, | Incubation Conditions, 35° C.; MICs read at 18-22 hours; Cation-Adjusted Mueller Hinton (CAMHB; BBL); Inoculum = $10^5$ CFU/mL |
| Strep. pneumoniae: | Incubation Conditions, 35° C.; MICs read at 22-24 hours; Cation-Adjusted Mueller Hinton + 2.5% Lysed Horse Blood (LHB); Inoculum = $10^5$ CFU/mL |
| Haemophilus influenzae: | Incubation Conditions, 35° C.; MICs read at 18-22 hours; Haemophilus Test Medium (HTM; Remel); Inoculum = $10^5$ CFU/mL |
| Candida: | Incubation Conditions, 35° C.; MICs read at 24 hours; RPMI 1640 Medium (BioWhittaker) Inoculum = $10^3$ CFU/mL |

Highest Concentration of Antibiotic Tested = 64 μg/mL (when starting from a 1 mg/mL sol'n in 50% DMSO)
Final Concentration of DMSO per well = 3.2%

Selection and Maintenance of Isolates

The strains used are isolates from either the Merck Culture Collection, the Merck Clinical Culture Collection or from Clinical Trials. The strain of *Haemophilus influenzae* is a mouse pathogen used for in vivo testing at Merck. The *Escherichia coli* strain is a cell wall permeable strain. The *Candida albicans* strain is used as a control. These culture are maintained as frozen stocks at −80° C. in a.) Microbank beads; b.) 2× Skim Milk; or c.) in 2× Trypticase Soy Broth+ 15% glycerol/50% horse serum (*Haemophilus* and *Streptococcus pneumoniae*).

Inoculum Preparation

Selected isolates are subcultured onto either Chocolate Agar Plates (*Haemophilus influenzae*), onto Trypticase Soy+ 5% Sheep Blood Agar Plates (*Streptococcus pneumoniae, Staphylococcus aureus, Escherichia coli, Enterococcus, Bacillus*) or onto Sabouraud Dextrose Agar (*Candida*) and incubated at 35° C. *Haemophilus* and *Streptococcus pneumoniae* are incubated in 5% $CO_2$; all other isolates are incubated in ambient air. Isolates are subcultured 2× before assay.

Colonies are selected from plates and used to prepare an inoculum equivalent to a 0.5 McFarland standard in Trypticase Soy Broth. An inoculum with a density equivalent to a 1.0 McFarland standard is prepared for *Streptococcus pneumoniae*. The inoculum density for all cultures is ~$10^8$ CFU/mL in TSB. This TSB inoculum is diluted 1:10 in sterile saline (4 mL inoculum+36 mL saline; equivalent to ~$10^7$ CFU/mL) and kept on ice until used to inoculate microtiter plates.

Colony counts are performed on randomly-selected isolates to confirm CFU/well (TSB inoculum plated out $10^{-5}$, $10^{-6}$ onto either TSA II+5% SB or onto chocolate agar plates, incubated overnight, 35° C., $CO_2$)

Plate Filling

All wells of 96-well microtiter plates (Dynex) are filled with 100 TL media. *Haemophilus* test media plates are prepared to test *Haemophilus influenzae*; Cation-Adjusted Mueller Hinton+5% Lysed Horse Blood plates are prepared to test *Streptococcus pneumoniae*; Cation-Adjusted Mueller Hinton Broth plates are prepared to test *Enterococcus, Staphylococcus aureus, Escherichia coli* and *Bacillus subtilis*. RPMI 1640 is used to test *Candida* The MICs against *S. aureus* Smith are determined in Cation-adjusted Mueller Hinton and in Cation-Adjusted Mueller Hinton+50% Human Serum to determine if the compound is inactivated by some component in serum (indicated by an increase in the MIC). Filled plates are wrapped in plastic bags (to minimize evaporation), stored frozen and thawed before use.

diluted to 1 mg/mL in a 1:1 dilution of DMSO/2×CAMHB (final concentration=50% DMSO/50% CAMHB). Compounds are serially diluted 1:1 in 50% DMSO/50% CAMHB in BD Biosciences Deep Well Polypropylene 96 well plates (starting concentration 1 mg/mL).

Microbroth Dilution Assay

Using a Finn Automated Multichannel Pipette, (0.5-10 μL volume) 6.4 TLs of antimicrobial working solutions are added to wells of filled microtiter plates (concentration of antimicrobial in first well=64 microg/mL; concentration of DMSO=3.2%). Antimicrobials are added in this manner to keep constant the amount of DMSO in each well (to keep compounds solubilized and to account for the possibility of non-specific killing by the DMSO. The last row contains a growth control of 3.2% DMSO.

With each assay, controls are run. They are Penicillin G and Chloramphenicol, prepared in the same manner as the compounds. Ertapenem is included as a control for the serum protein binding assay.

Plate Inoculation

All wells of microtiter plates are inoculated with (saline-diluted) culture using the MIC 2000 System, an automated plate inoculating device which delivers an inoculum of 1.5 TL per well. Plates are incubated at 35° C. in ambient air. An uninoculated plate is also incubated as a sterility check. Results are recorded after 22-24-hours' incubation. Plates were read to no growth. The MIC is defined as the lowest antimicrobial level which resulted in no growth after 22-24-hours' incubation.

Compound I demonstrates antibacterial activity against various strains of *S. aureus, E. faecalis, E. faecium, B. subtilis, S. pneumoniae* and *E. coli*. Compound I also demonstrates antibacterial activity against various species that are resistant to many known antibiotics such as methicillin-resistant *S. aureus* (MRSA), vancomycin-resistant *Enterococcus* sp. (VRE), multidrug-resistant *E. faecium*, macrolide-resistant *S. aureus* and *S. epidermidis*, and linezolid-resistant *S. aureus* and *E. faecium*. The minimum inhibitory concentration (MIC) values for these test strains range from 0.1 to 32 ug/mL. MICs are obtained in accordance to the NCCLS guidelines.

What is claimed is:

1. An isolated compound of structural formula (I):

(I)

or a pharmaceutically acceptable salt thereof.

2. A process for the preparation of an isolated compound of structural formula (I):

(I)

which comprises the cultivation of a *Streptomyces* sp. with ATCC# PTA-5316 (MA7327) or ATCC#PTA-5317 (MA7331) or a natural mutant thereof in a nutrient medium and isolating the Compound (I) from the fermentation broth.

3. The process of claim 2 wherein the fermentation is conducted at a temperature of about 10° C. to about 40° C.

4. The process of claim 3, wherein the fermentation is conducted at a temperature of about 28° C.

5. A pharmaceutical composition comprising a pharmaceutically acceptable carrier and an effective amount of a compound of structure (I) according to claim 1.

* * * * *

SEQUENCE LISTING

<160> NUMBER OF SEQ ID NOS: 2

<210> SEQ ID NO 1
<211> LENGTH: 1449
<212> TYPE: DNA
<213> ORGANISM: Streptomyces sp.

<400> SEQUENCE: 1

| | | | | | | |
|---|---|---|---|---|---|---|
| ccgtcaggac | ggacgctggc | ggcgtgctta | acacatgcaa | gttccaacga | tgaacctcct | 60 |
| tcgggagggg | aattagtggc | gaacgggtga | gtaacacgtg | ggcaatctgc | ccttcactct | 120 |
| gggacaagcc | ctggaaacgg | ggtctaatac | cggatacgac | caccgaccgc | atggtcgtgg | 180 |
| tggtggaaag | ctccggcggt | gaaggatgag | cccgcggcct | atcagcttgt | tggtggggtg | 240 |
| atggcctacc | aaggcgacga | cgggtagccg | gcctgagagg | gcgaccggcc | acactgggac | 300 |
| tgagacacgg | cccagactcc | tacgggaggc | agcagtggga | aatattgcac | aatgggcgaa | 360 |
| agcctgatgc | agcgacgccg | cgtgagggat | gacggccttc | gggttgtaaa | cctctttcag | 420 |
| cagggaagaa | gcgagagtga | cggtacctgc | agaagaagcg | ccggctaact | acgtgccagc | 480 |
| agccgcggta | atacgtaggg | cgcaagcgtt | gtccggaatt | attgggcgta | aagagctcgt | 540 |
| aggcggcttg | tcacgtcgga | tgtgaaagcc | cggggcttaa | ccccgggtct | gcattcgata | 600 |
| cgggcaggct | agagttcggt | aggggagatc | ggaattcctg | gtgtagcggt | gaaatgcgca | 660 |
| gatatcagga | ggaacaccgg | tggcgaaggc | ggatctctgg | gccgatactg | acgctgagga | 720 |
| gcgaaagcgt | ggggagcgaa | caggattaga | taccctggta | gtccacgccg | taaacgttgg | 780 |
| gaactaggtg | tgggcgacat | tccacgtcgt | ccgtgccgca | gctaacgcat | taagttcccc | 840 |
| gcctggggag | tacggccgca | aggctaaaac | tcaaaggaat | tgacggggc | ccgcacaagc | 900 |
| agcggagcat | gtggcttaat | tcgacgcaac | gcgaagaacc | ttaccaaggc | ttgacataca | 960 |
| ccggaaacgt | ctggagacag | gcgccccctt | gtggtcggtg | tacaggtggt | gcatggctgt | 1020 |
| cgtcagctcg | tgtcgtgaga | tgttgggtta | agtcccgcaa | cgagcgcaac | ccttgttctg | 1080 |
| tgttgccagc | atgcccttcg | gggtgatggg | gactcacagg | agactgccgg | ggtcaactcg | 1140 |
| gaggaaggtg | gggacgacgt | caagtcatca | tgccccttat | gtcttgggct | gcacacgtgc | 1200 |
| tacaatggcc | ggtacaatga | gctgcgatac | cgcgaggtgg | agcgaatctc | aaaaagccgg | 1260 |
| tctcagttcg | gattggggtc | tgcaactcga | ccccatgaag | tcggagttgc | tagtaatcgc | 1320 |
| agatcagcat | tgctgcggtg | aatacgttcc | cgggccttgt | acacaccgcc | cgtcacgtca | 1380 |
| cgaaagtcgg | taacacccga | agccggtggc | cacaacgccc | tctgtgcgag | gcaatctgtc | 1440 |
| cgaaggtcg | | | | | | 1449 |

<210> SEQ ID NO 2
<211> LENGTH: 1496
<212> TYPE: DNA
<213> ORGANISM: Streptomyces sp.

<400> SEQUENCE: 2

| | | | | | | |
|---|---|---|---|---|---|---|
| tcctggctca | ggacgaacgc | tggcggcgtg | cttaaacaca | tgcaagtcga | acgatgaacc | 60 |
| tccttcggga | gggattact | ggcgaacggg | tgagtaacac | gtgggcaatc | tgcccttcac | 120 |
| tctgggacaa | gccctggaaa | cggggtctaa | taccggatac | gacacacgac | cgcatggtct | 180 |
| gtgtgtggaa | agctccggcg | gtgaaggatg | agcccgcggc | ctatcagctt | gttggtgggg | 240 |
| tgatggccta | ccaaggcgac | gacgggtagc | cggcctgaga | gggcgaccgg | ccacactggg | 300 |

```
actgagacac ggcccagact cctacgggag gcagcagtgg ggaatattgc acaatgggcg    360
aaagcctgat gcagcgacgc cgcgtgaggg atgacggcct tcgggttgta aacctctttc    420
agcagggaag aagcgagagt gacggtacct gcagaagaag cgccggctaa ctacgtgcca    480
gcagccgcgg taaataacgt agggcgcaag cgttgtccgg aattattggg cgtaaagagc    540
tcgtaggcgg cttgtcacgt cggatgtgaa agcccggggc ttaacccegg gtctgcattc    600
gatacgggca ggctagagtt cggtagggga gatcggaatt cctggtgtag cggtgaaatg    660
cgcagatatc aggaggaaca ccggtggcga aggcggatct ctgggccgat actgacgctg    720
aggagcgaaa gcgtggggag cgaacaggat tagatacect ggtagtccac gccgtaaacg    780
ttgggaacta ggtgtgggcg acattccacg tcgtccgtgc cgcagctaac gcattaagtt    840
ccccgcctgg ggagtacggc cgcaaggcta aaactcaaag gaattgacgg gggcccgcac    900
aagcagcgga gcatgtggct taattcgacg caacgcgaag aaccttacca aggcttgaca    960
tacaccggaa acgtctggag acaggcgccc ccttgtggtc ggtgtacagg tggtgcatgg   1020
ctgtcgtcag ctcgtgtcgt gagatgttgg gttaagtccc gcaacgagcg caacccttgt   1080
tctgtgttgc cagcatgccc ttcggggtga tggggactca caggagactg ccggggtcaa   1140
ctcggaggaa ggtggggacg acgtcaagtc atcatgcccc ttatgtcttg ggctgcacac   1200
gtgctacaat ggccggtaca atgagctgcg ataccgcgag gtggagcgaa tctcaaaaag   1260
ccggtctcag ttcggattgg ggtctgcaac tcgacccat gaagtcggag ttgctagtaa    1320
tcgcagatca gcattgctgc ggtgaatacg ttcccgggcc ttgtacacac cgcccgtcac   1380
gtcacgaaag tcggtaacac ccgaagccgg tggcccaacc ccttgtggga gggaatcgtc   1440
gaaggtggga ctggcgattg ggacgaagtc gtaacaaggt agccgtaccg gaaggt        1496
```